United States Patent [19]

Wade

[11] Patent Number: 4,798,207

[45] Date of Patent: Jan. 17, 1989

[54] DEVICE FOR ENABLING TIME-INTEGRATED MEASUREMENT OF SUBSTANCES IN BIOLOGICAL FLUIDS

[76] Inventor: Stephen E. Wade, 1720 So. Marshall Rd., #50, Boulder, Colo. 80303

[21] Appl. No.: 858,736

[22] Filed: May 2, 1986

Related U.S. Application Data

[62] Division of Ser. No. 492,705, May 9, 1983, Pat. No. 4,594,326.

[51] Int. Cl.$^4$ ............................................... A61B 5/00
[52] U.S. Cl. .................................... 128/632; 128/633; 128/635; 128/637; 128/765; 604/175; 604/891.1; 604/892.1
[58] Field of Search ...................... 604/892, 175, 891.1, 604/892.1; 128/632, 633, 635, 637, 768; 436/501

[56] References Cited

U.S. PATENT DOCUMENTS 3,518,982 7/1970 Timmins et al.
3,993,072 11/1976 Zaffaroni.
4,016,864 4/1977 Sielaff et al.
4,220,152 9/1980 Dresback.
4,325,388 4/1982 Bucalo.

OTHER PUBLICATIONS

Goldzieher et al., Journal Clinical Endocrinology & Metabolism, 43:824 (1976).
Zadik et al., Journal of Clinical Endocrinology & Metabolism, 51:1099 (1980).
Lasnitzki and Franklin, Journal of Endocrinology, 64:289 (1975).
Vermeulen et al., Journal of Endocrinology & Metabolism, 33:759 (1971).
Kowarski et al., Journal Clinical Endocrinology and Metabolism, 32:356 (1971).
Schellman et al., Journal of the American Chemical Society, 76:2808 (1954).
Seal and Doe, Steroids 5:827 (1965).
Ballard et al., Journal Clinical Endocrinology & Metabolism, 41:290 (1975).
Goode, British Journal of Pharmocology, 41:558 (1971).
Cheesman et al., Fertility and Sterility, 38:475 (1982).

Primary Examiner—Sidney Marantz
Attorney, Agent, or Firm—Robert E. Harris

[57] ABSTRACT

A device for enabling a measurement of the time integral of concentrations of substances in a biological fluid, without the necessity to collect samples of that fluid, is disclosed for accomplishing time-integrated measurement of the freely-diffusable fraction of substances of interest by providing conditions under which the rate of accumulation of such substances by the device placed in intimate contact with the biological fluid is at all times proportional to their concentration.

18 Claims, 1 Drawing Sheet

U.S. Patent   Jan. 17, 1989   4,798,207
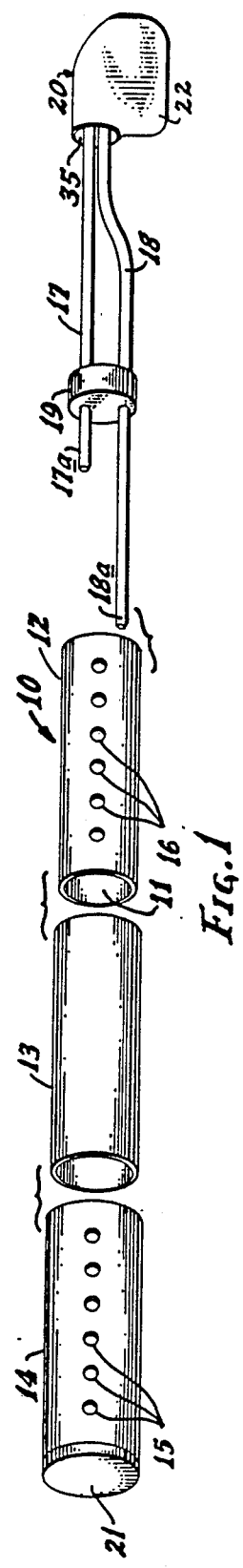
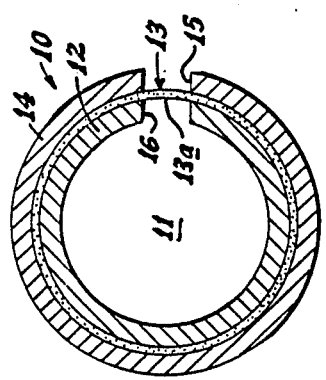
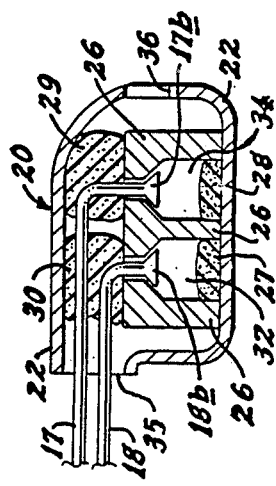

DEVICE FOR ENABLING TIME-INTEGRATED MEASUREMENT OF SUBSTANCES IN BIOLOGICAL FLUIDS

RELATED INVENTION

This application is a division of U.S. application Ser. No. 06/492,705, filed May 9, 1983, and issued on June 10, 1986 having U.S. Pat. No. 4,594,326, entitled Time-Integrated Measurement Means and Method for Substances in Biological Fluids.

FIELD OF THE INVENTION

This invention relates to a device for obtaining an estimate of the time integral of the concentration of a substance in a biological fluid.

More particularly, it relates to a device for obtaining, for assay, a single aliquot of material, in which the content of the substance of interest provides a direct measure of the time integral of the concentration of the freely-diffusable fraction of that substance in the biological fluid over a known time interval.

BACKGROUND OF THE INVENTION

Very often a primary goal in making measurements of substances in biological fluids is to provide information about some enduring state of the organism which produces those fluids, such as when biochemical measures are taken to provide information for the diagnosis of disease.

It often happens that the concentrations of these substances in the biological fluids are subject to temporal fluctuations, such that a series of samples taken from the biological fluids would reveal a distribution of concentration values. Generally it is not the concentration present at a given instant, but rather the extended summation of the fluctuating concentrations over some time interval, which is of ultimate interest. This summation of instantaneous levels over a defined time interval, in mathematical terms, would be called the "time-integral".

The time-integral is preferred because it is more representative of the enduring state of the organism than are the temporally-fluctuating instantaneous values. The time integral, divided by the length of the time interval over which it was obtained, is equivalent to the true average concentration of the substance over that interval.

This advantage of the time-integral over instantaneous values is illustrated by Goldzieher et al (*Journal of Clinical Endocrinology and Metabolism* 43:824 (1976)). These authorities estimated the 8-hour mean of blood plasma luteinizing hormone concentrations in normal men by a prior art method (described below), then calculated the probability that a single plasma sample would yield a value within plus or minus 20 percent of this mean.

They estimated this probability was only 30%, i.e., that a single plasma measurement was a very poor indicator of the enduring state of the organism, with regard to this important substance.

The practical diagnostic advantage of time-integrated measurement can be illustrated by another example from the medical literature. Zadik et al (*Journal of Clinical Endocrinology and Metabolism* 51:1099, (1980)) compared the ability of three clinical tests to distinguish among three classes, i.e., normal persons, patients with mild essential hypertension, and patients with Cushing's syndrome. Three tests were used for each of those three classes of patients: (1) a prior-art method (described below) of estimating the time integral of plasma cortisol, (2) measurement of urinary free cortisol, and (3) measurement of urinary 17-hydroxycorticosteroids. The latter two methods are recognized to be far superior to instantaneous plasma cortisol measurement, and are considered to be the standard measures in current medical practice.

However, the time-integrated plasma cortisol measurement was found to be clearly superior to the standard measures in discriminating among these groups. The authors nevertheless declined to recommend the time-integrated measurement as a new standard of practice, however, because the prior art heretofore available for that improved method is exceedingly complex.

It often happens that compounds of biological interest (e.g., hormones, drugs, amino acids, etc.) exist in biological fluids in two states or fractions, i.e., those molecules which are in association with macromolecules (generally proteins) such that their movements and reactions are in some way limited by the macromolecules, and those which are free of such association.

The latter fraction is often called the "free" fraction and the former the "bound" fraction; and in general, the proportion of the bound and free fractions is determined by the concentrations of the various biochemical components of the biological fluid, by temperature, and by other factors of a physical or chemical nature.

When the compounds of interest exist in both "bound" and "free" states, it is often observed that the biological effects of the compounds seem to be exerted only by the free fraction (see, for example, Lasnitzki and Franklin, *Journal of Endocrinology* 64:289, (1975)).

Indeed, it is found that the free fraction concentration of a hormone in a biological fluid is a much better indicator of the state of the organism than is the total concentration. Vermeulen et al (*Journal of Endocrinology and Metabolism* 33:758, (1971) present many cases illustrating the superiority of measurements of free testosterone concentration obtained by a prior art method (described below), over simple measurement of the total hormone concentration, again in the context of medical diagnosis.

Essentially, the prior art as to the measurement of the time-integral of substances in biological fluids consists of two similar means and methods. As now described, they are seen to both fail to achieve the advantages of the present invention, and, instead, both require the removal of samples or specimens over a prolonged time period, and other differences as noted herein.

The means and method described by Kowarski et al (*Journal Clinical Endocrinology and Metabolism* 32:356, (1971)) is typical of those using a prolonged sample-removal procedure, this type being a constant-withdrawal system (U.S. Pat. No. 3,908,657) to obtain a sample.

In the Kowarski system, a mechanical pump is used to obtain a sample of the biological fluid at a constant rate over a long time interval. The content of the relevant substance in the sample is then measured by suitable means; and since each instant of the elapsed interval is represented by an equal amount of fluid in the sample, the concentration of the compound of interest in the whole sample directly reflects the time integral of its concentration in the biological fluid over the pumping interval. This is similar to the method employed by Zadik et al (1980).

In practice, this system has several disadvantages, relative to the invention to be described here, and the disadvantages are now summarized.

First, the Kowarski system involves the use of a miniaturized precision pump which is very expensive to manufacture, relative to the device of the invention to be described.

Second, a very bothersome disadvantage is that a specially-treated catheter must be inserted in a major blood vessel of the subject, and maintained without thrombosis for the duration of the measurement procedure; this requirement makes the practice of the Kowarski invention stressful for some if not most subjects and even impossible for others (such as some animals which will not tolerate the externalized catheter connection).

Third, the continuing sample-removal procedure of the prior art has the disadvantage that the necessity to avoid thrombosis in the catheter places limits on the slowness with which blood can be withdrawn, and places limits upon the duration of the sampling period; and these limits are so restrictive that small animals (such as laboratory rats) are not suitable subjects due to their limited blood volume, and most subjects cannot reliably be monitored for more than 24 hours without changing catheters.

Fourth, as a disadvantage, and even if the other obvious bothers and distress to the subject were not present, the subject must either be severely limited in its movements, or else must carry the pump and associated apparatus along with it by some means.

Fifth, this prior art method has been applied only to blood.

A second means and method shown in the prior art, also of prolonged sample-removal nature, is typified by the method of Goldzieher et al (1976). In that method, multiple instantaneous samples are obtained frequently and at regular intervals throughout the measurement period. The concentration of the compound of interest is measured by suitable means in each sample, and the results are then mathematically integrated to yield an estimate of the time integral.

That prior art method, because it too is of course of prolonged sample-removal type even though of repetitive rather than continuous nature, shares many disadvantages with the previously described prior art, and is generally more laborious, as will be apparent when it is considered that either a catheter must be maintained as before, or repeated blood samples otherwise drawn, and that a large number of samples of the blood plasma must be measured by suitable means, thus more disadvantageous in this respect than the Kowarski system described above in which a single pooled sample was involved.

The prior art as to measurement of the free fraction of biochemical substances consists of a number of devices for accomplishing a physical separation of the macromolecules which bind the compounds of interest, from some remaining part of the sample, without seriously disturbing the proportion of the bound and free fractions. All such prior art devices fail to provide advantages of the present invention, in that they require further procedures in addition to that of an already complex analysis.

Among the oldest methods is equilibrium dialysis, as shown in Schellman et al, *Journal of the American Chemical Society* 76:2808 (1954), in which is used a membrane which permits the passage of the free compound of interest, but not the macromolecules and the associated bound compound. The membrane is arranged so that it serves as a differentially-permeable barrier between the sample with its bound and free fractions, and a small volume of a similar fluid, which contains neither the macromolecules nor the bound or free portions of the compound of interest.

With this type of device, substances which can pass through the membrane do so in accordance with the laws of diffusion; and eventually an equilibrium is reached wherein the concentration of the "free" compound of interest is equal on both sides of the membrane, while the macromolecules on the "sample" side of the membrane continue to sequester the "bound" fraction.

The small volume containing only "free" compound is then removed and the total concentration therein measured by suitable means, thus yielding an estimate of "free" compound concentration in the original sample.

Other methods in the prior art accomplish the separation of macromolecules by causing them to be insoluble in the fluid without causing them to release the "bound" molecules. The means for making the macromolecules insoluble differ from one case to another, but generally involve the introduction of chemical species which combine with the macromolecules to produce an insoluble complex, which is an additional step not required by the present invention.

Perhaps the advantages and significant nature of the inventive concepts set forth herein may be realized by reference to recent advances in related art, which yet fail to accomplish the achievements in this invention. Cheesman et al (*Fertility and Sterility* 38:475, (1982)) have reported a method whereby a binding preparation is implanted in an animal, for the purpose of binding and sequestering a circulating hormone and depleting its concentration throughout the blood plasma of the animal. This art differs from the present invention in that the pathway, by which the hormone has access to the binding protein, has unknown and non-constant permittivity, so that no useful measurement can be obtained thereby.

Further, this related art is designed expressly to deplete and change the level of the hormone, and thereby to preclude useful measurement.

This present invention, quite in contrast, avoids depletion of, and allows measurement of, the time integrals of compounds such as hormones, by virtue of a pathway of precisely known constant, and limited permittivity.

Similarly, Goode (*British Journal of Pharmacology* 41:558, (1971)) has described a device somewhat superficially similar to that preferred in the present embodiment of this invention, but the Goode device is neither designed for, nor suitable for use, in the practice of this invention. The Goode device incorporates a tubular reservoir, which communicates with its immediate environment through a single port of dialysis membrane installed at one end of the tubular reservoir, while at the other end two small tubes are fitted. Further, the Goode device is a subcutaneously-implanted reservoir for the chronic delivery of drugs, which operates by the diffusion of drugs from the reservoir, through the membrane, and into the surrounding environment. It is provided with externalized tubes for the purpose of replenishing the drugs contained in the reservoir.

SUMMARY OF THE INVENTION

The general object of the present invention is the provision of a novel device for obtaining a measurement of the time integral of the concentration of a biochemical substance in a biological fluid.

A more particular object of the present invention is the provision of such a device such that the measurement is confined to the time integral of the concentration of the "free fraction" of the biochemical substance, as previously defined.

A further object is the provision of such a device which does not require the collection of blood, and which is not limited in application to blood plasma.

Another object is the provision of such a device which produces a single aliquot of material in which the content of the substance of interest, when measured by suitable means, is a direct measure of the time integral of the free fraction of the said substance in the biological fluid, over a known time interval.

Still another object is the provision of such a device which is adapted to repeated measurements of that time integral within a single subject, as may be desired or required in some experimental procedures.

Yet another object is the provision of such a device which can be used to measure the said time integral over long or short periods of time, and in subjects which are free of any external restraint or encumbrance.

A further object is the provision of such a device which is adaptable to the measurement of that time integral of a great variety of biochemical substances.

A still further object is the provision of such a device which, by virtue of the cumulative nature of its operation, allows the measurement of the time integral of substances, which at any one instant is at such low concentration in the biological fluid as to be unmeasurable by present devices.

With these and other objects in view, which will become apparent to one skilled in the art as the description proceeds, this invention resides in the novel construction, combination, and arrangement of parts substantially as hereinafter described, and more particularly defined by the appended claims it being understood that changes in the precise embodiment of the herein disclosed invention are meant to be included as come within the scope of the claims.

BRIEF DESCRIPTION OF THE DRAWINGS

The accompanying drawings illustrate a complete embodiment of the invention according to the best mode so far devised for the practical application of the principles thereof, and in which:

FIG. 1 is a pictorial, generally exploded view of a present invention;

FIG. 2 is a longitudinal sectional view, in larger scale, of the external-connector portion of the device shown in FIG. 1, showing details of its construction; and FIG. 3 is a transverse cross-sectional view through the main body of the device, showing the arrangement of the three layers of the device's construction, but with its components no longer in the exploded-view condition.

DESCRIPTION OF THE INVENTION

Part of the invention is the discovery that when a fluid containing certain substances capable of binding the substances of interest is contained within a device, which is constructed so as to allow diffusion of the substances of interest in their "free" form from outside the device to inside at a precisely controlled rate, yet able to contain these certain substances capable of binding the substance of interest within the device, and when such a device containing such a fluid is installed in intimate contact with the biological fluid, with a means provided for recovering the contents of the device after some time has elapsed, and the content of the substance of interest present at that time in the recovered fluid is measured by suitable means, that the several advantageous achievements of the present invention are realized.

The device will be explained using as an illustrative example the particular case of an embodiment of the invention presently preferred for measuring the time integral of the free fraction of the hormone corticosterone, in the interstitial fluid of laboratory rats.

However, it will be understood that many modifications of particulars of the embodiment preferred for this purpose may be made, without departing from the novel concepts of this invention.

Illustrative of some modifications which are preferred when the invention is used for other purposes, are set forth herein also, so that it will be readily understood how all the objects and attainments of the invention are achieved by modifications within these concepts herein set forth.

The present invention involves the creation and maintenance of conditions within an implanted device, such that the rate of diffusion of the free fraction of the compound of interest from the body fluids surrounding the implanted device, into the device itself, is a known function of the concentration of the free fraction of that compound in the body fluid which is in intimate contact with the device.

These conditions are created and maintained by providing, at the inside of the implanted device, a fluid-filled compartment in which the concentration of the free fraction of the compound of interest is maintained at a very small value relative to its concentration outside the device.

This interior fluid-filled compartment communicates with the biological fluid in which the implant resides, across a layer of material which provides a pathway of known and constant permittivity for the diffusion of the compound of interest in its free form, but which is essentially impermeable to macromolecule-bound forms and to macromolecules in general.

The arrangement of these features will be more apparent by reference to the device 10 as shown in FIG. 3, in which the interior fluid-filled compartment 11 communicates with the device's immediate environment through the differentially-permeable membrane 13, which is held in place between the compartment 11 and the environment by virtue of its juxtaposition between rigid shell 12 and outer shell 14, and which comprises the only barrier to free transfer of material between the compartment 11 and the environment in the region defined by a row of apertures 15 in shell 14 and a corresponding row of apertures 16 in the shell 12.

The region 13a defined by one set of corresponding apertures 15 and 16 in which membrane 13 is exposed will hereafter be referred to as a "diffusion port", and it will be noted that the apertures 15 and 16 of the two rows are correspondingly spaced along each row, and that corresponding ones of each of the apertures 15 and 16 are in registry when the shells 12 and 14 are in assembled condition.

When components 12, 13 and 14 are assembled, in contrast to their "exploded-view" showing in FIG. 1, the device 10 provides a sealed compartment 11 having multiple diffusion ports 13a, each like the one shown in FIG. 3 and with a means provided for recovering the contents of the sealed compartment 11 without removing it from the animal, as is more further described below.

The means of maintaining the concentration of the free compounds of interest at a very small value, as indicated above as being required, will differ depending upon the compound to be measured, but in general this requirement is met by providing a solution or suspension of a protein which is able to form a high-affinity complex with the compound of interest, such that the complexed form is not available for diffusion across the differentially-permeable membrane.

In the illustrative case of corticosterone, many such proteins are known in the related arts, including but not limited to plasma corticosteroid binding globulins (Seal and Doe, *Steroids* 5:827 (1965)), immunoglobins having affinity for corticosterone, and corticosteroid receptor proteins (Ballard et al, *J. Clin. Endo. Metab.* 41:290 (1975)).

In the presently preferred embodiment of the invention, there is used blood serum of rats, which contains rat corticosteroid binding globulin and from which endogenous steroids have been removed by incubation with charcoal.

The choice of the binding preparation is a matter of convenience among preparations having the desired binding property, and the use of another binding preparation, including even a non-protein binder, is not outside the novel concepts of this invention.

The binding preparation is used to maintain the concentration of the free fraction of the compound of interest inside the device at a low value relative to its concentration in the environment of the device, as required above. A low value is recognized as one which does not result in significant reduction in the rate of diffusion across the differentially-permeable membrane, when the environmental concentration of the free fraction is at its minimal expected value, compared to the rate which would exist if the concentration inside the device were zero.

Recognition of what constitutes a low value thus requires knowledge of the minimal expected concentration of the compound of interest in the environment, and judgment as to what constitutes a significant reduction in rate of diffusion. If the level of the free fraction inside the device becomes too high, the estimate of the time-integral of free concentrations obtained by use of this invention will be an underestimate. Thus while it may still be extremely useful, the estimate will not be a true time integral.

In the present embodiment of the invention preferred for measurement of the time integral of corticosterone in rats, the length of time over which the integration is performed is regulated so that the level of free corticosterone inside the implant does not exceed a value which would decrease the rate of diffusion by 10% at an environmental concentration of 5 nanograms/milliliter.

Use of other operating criteria, even including deliberate operation so as to obtain an underestimate, is not outside the novel concepts of this invention.

The differentially-permeable membrane used in the presently preferred embodiment of this invention is of a type well-known in the related arts, being standard cellulose dialysis membrane with a molecular weight cutoff of 12,000–14,000 daltons.

The choice of material for the differentially-permeable layer is a matter of convenience and may vary according to the application. The use of other types of cellulose membrane, of other synthetic or natural materials, and even of substantially intact membranes from organisms, is not outside the novel concepts of this invention.

As shown in FIGS. 1 and 3, the main compartment of the device is defined by rigid shell 12, which is covered in successive layers by membrane 13 and outer shell 14, which outer shell is plugged at one end by a cap 21.

At the opposite end of the outer shell 14, the means for exchanging the contents of the device is inserted, which means is shown in FIG. 1. The exchange means consists of tubes 17 and 18 fixed and sealed in plug 19, which tubes 17 and 18 project to open ends, respectively 17a and 18a, in the interior compartment 11, and also to open ends 17b and 18b in a septum block 20. The exchange means is inserted so that plug 19 seals within shell 12, sealing that end of the shell 12.

FIG. 2 shows the detailed construction of the septum block 20 with the tubes 17 and 18 flared at their ends, respectively 17b and 18b, and secured by means of a silicone rubber sheath 22 stretched tightly around wall members 26 within the septum block 20.

Silicone rubber sealer is placed at locations 27, 28, 29 and 30 providing at each location a seal member which provides or assures a leakproof seal and allows repeated penetration at locations 27 and 28 by needles, so that fluid introduced through a needle at 27 travels through tube 18 and inner compartment 11 before exiting through tube 17 and a needle inserted through body 28. The material of the sheath 22 permits repeated puncturing.

Since the sealant bodies 27, 28, 29 and 30 effectively close the chambers 32 and 34, which respectively provide portions of the inlet and outlet passageways, the end openings 35 and 36 need not be closed.

It will readily be appreciated that if tubes 17 and 18 are externalized through the skin of an animal, having the device's assembled shells 12, 13 and 14 subcutaneously implanted and with the septum block 20 exposed in an easily accessible position, then, by the procedure just described, the contents of the compartment 11 can be recovered with only minimal disturbance of the animal.

Components 14, 21, and 22 are silicone rubber in the presently preferred embodiment of the invention, while the other parts (excluding the cellulose dialysis membrane 13) are desirably of polyethylene. This choice of materials is well known in the prior art of implantable devices. However, construction of the device using other materials, or with some parts fused or made integral, is not to be regarded as outside the concepts of the present invention.

For example, simplified construction in which the walls of the device are made of a single homogeneous layer of material, which varies in thickness so as to provide some regions having higher permittivity, those regions thus taking on the functional character of diffusion ports, is within the concepts. Similarly, a construction having walls of uniform thickness and homogeneous composition may be given the desired functional properties by regionally applying a treatment which alters the permittivity of the material, as by enzymatically reducing the degree of crosslinking in a cellulose construction, thereby increasing its permittivity.

Similarly, the geometric form and arrangement of the diffusion ports can vary from that shown without departing from the novel concepts of the present invention so long as a distribution of the areas permittive of diffusion over the surface of the device is maintained.

Likewise, increasing or decreasing the surface area of the diffusion ports, which has the effect of regulating the rate at which the device accumulates the compound of interest, is entirely within the scope of the present invention. Likewise, use of such a device, which lacks the means for conveniently removing the fluid from the compartment without removing the device from the animal, is within the novel concepts of the present invention.

When the invention is practiced as just described, it is found that the content of the compound of interest in the fluid recovered from the device, when measured by suitable means, is proportional to the time integral of the concentration of the free fraction of the substance of interest in the immediate environment of the device.

The constant of proportionality is determined by similarly practicing the invention, using as the environment of the device an artificially prepared solution having known concentration of the free fraction of the compound of interest at all times, as will be apparent to one skilled in the art.

It will readily be appreciated that this invention accomplishes these achievements previously specified: measurement of the time integral of a substance in a biological fluid, more particularly of the free fraction of that substance, the measurement being without necessity of the collection of blood, and by the final determination of the content of the substance in a single aliquot of fluid; that measurement being by a device which is adapted to repeated measurements within a single subject.

It will further be seen that the invention is adaptable to the measurement of any substance, for which both a binding preparation, and a material capable of acting as a membrane permitting diffusion of the free form but not the bound form of the substance, can be found.

Further, it will be seen that by use of a binding preparation of high capacity, the time interval over which the integration is accomplished can be extended over many hours or days, so long as the concentration of the free compound inside the device remains low, as previously discussed.

In addition, it will be recognized that the invention can be practiced so as to accomplish these objects with application to various biological fluids such as interstitial fluid, blood plasma, cerebrospinal fluid, lymph, etc., and also to fluids not contained within an organism, such as fluids produced by microbial fermentation or enzyme reaction in industrial processes.

Further it will be seen that the invention may be practiced with a device which has no parts external to the subject in which it is installed, so that while not optimally suited to repeated measurements within one subject, such a practice leaves the subject free of any external restraint or encumbrance.

Finally it will be seen that this invention is applicable in the measurement of the time integral of the concentration of substances without regard to their instantaneous concentrations, so that even through the instantaneous concentrations may be so low as to be measurable by some known means, yet the integral of these concentrations over some time may be readily measurable by this same means.

Two prominent features which distinguish the device used in the presently preferred embodiment of this invention, from this related art, are first, the number and spatial arrangement of the diffusion ports, and second, the provision of a means of rapidly exchanging the contents of the device with minimal disturbance to the animal.

First, the dispersal of numerous diffusion ports over the lateral surface of the device is found to promote precisely reproducible rates of uptake of the substance of interest, while reliance upon a single port at the end of the device is found to give imprecise and non-reproducible results, presumably because of local depletion of the concentration of the substance of interest and unfavorable interactions with tissue in the case of the single-port device.

The innovation of using multiple dispersed ports of small size avoids the problem of local depletion, since the rate of uptake at each small port is quite low relative to the rate at which the affected volume of biological fluid equilibrates with its sources.

This same innovation insures that, although each small port individually may provide a rate of uptake higher or lower than average, due to tissue interactions, still the sum of the several rates will be much less variable than the rate of a single port, which is likewise liable to yield a rate either higher or lower than average in each installation.

This fact will be recognized to follow by analogy to the finding in the science of statistics, that the variance of the mean of n observations drawn from a population, will be $\sigma^2/\sqrt{n}$, while the variance associated with each observation individually is $\sigma^2$.

As to the dispersion and number of the diffusion ports 13a, it has been found that they should be of significantly scattered nature, i.e., that no more than one-half of the surface area of the port or ports is contained in a square region as small as one-tenth of the entire surface area of the wall means. This assures avoidance of local depletion (as discussed above) and assures a less-variable rate of uptake than with a single diffusion port. The effect of the specification of a square region is to require, no matter what portion of the total area of the wall means is accounted for by ports, that the ports should be dispersed over a significant portion of the total area of the wall means, e.g., that even if the area of ports accounts for only 1/100 the area of the wall means, still no accident, which resulted in blockade of all the ports in a square area as large as 1/10 of the entire surface of the device, could reduce the available area of ports by more than one-half.

Second, it is often important in practicing the present invention to avoid, so much as possible, the profound changes in the levels of substances which occur when the animal subject is handled or restrained. The innovation of providing the septum block, as a means for making connections necessary to service the implanted device quickly and without the necessity of restraining the animal, allows this object to be met.

With the device of the related art, immobilization of the animal is necessary in order for the practitioner to service the device, whereas, with the device of the presently preferred embodiment of this invention, immobilization is not practiced.

It is thus seen that this device for measurement of the time integral of concentration of chemical substances in biological fluids provides novel and advantageous concepts and features of operation and construction, including provision of a means including having diffusion ports permitting maintenance of accurate rate of diffusion, and including a remote connector permitting rapid and convenient service of the measurement means.

Accordingly, it will be seen from the foregoing description of this invention according to this illustrative embodiment, considered with the accompanying drawings, that the present invention provides a new and useful means of time-integral measurement of chemical substances in biological fluids, having desired advantages and characteristics, and accomplishing its intended objects, including those hereinbefore pointed out and others which are inherent in the invention.

What is claimed is:

1. A device for maintaining controlled diffusion of chemical substances of interest, comprising:
   wall means defining a compartment, said wall means being provided with one of a diffusion port and diffusion ports of limited permeability, said ports providing a region which is generally permeable to diffusion of said chemical substances of interest, the remainder of said wall means of said compartment being substantially impermeable to diffusion of said chemical substances of interest, the distribution of the surface area of said ports being of a scattered nature such that no more than one-half of said surface area of said ports is contained in a square region as small as one-tenth of the entire surface area of said wall means.

2. A device as set forth in claim 1, in which said permeable and impermeable portions of said compartment's wall means are provided by making said ports of significantly less thickness than are the other portions of said compartment's wall means, said permeable and impermeable portions both being of the same material.

3. A device as set forth in claim 1, in which said permeable and impermeable portions of said compartment's wall means are provided by differentially applying a physical or chemical treatment to an initially homogeneous material.

4. A device as set forth in claim 1, in which said permeable and impermeable portions of said compartment's surface are provided by constructing said impermeable regions of the wall means of the compartment of two or more juxtaposed layers of material, said layers when juxtaposed being substantially impermeable to diffusion of said chemical substances of interest, while constructing said permeable regions with fewer layers, the construction of said fewer layers being generally permeable.

5. A device as set forth in claim 4, generally in the form of a cylinder closed at both ends, with multiple ports distributed over its longitudinal surface, in which the differential permeability of said ports arises from the absence in the regions designated as said ports, and the presence elsewhere, of two layers of material having low permeability to diffusion of said chemical substances of interest, the surface of said device in the regions designated as said ports consisting of a third layer of material having higher permeability to diffusion of said chemical substances of interest, the spatial arrangement of said three layers being that of substantially co-axial cylindrical shells, with said third layer of material disposed between said two layers of material.

6. A device as set forth in claim 1, in which there is provided a means for removing and replacing the fluid contents of said compartment, said means comprising two tubes which project from said compartment to a remote location, and providing at said remote location wall means forming two closed chambers, each of said two tubes leading respectively to one of said chambers, a portion of said wall means of each of said chambers being provided with means permitting a flushing of said device by pressure means applied to one of said chambers and extraction means applied to the other of said chambers, whereby specimens of the contents of said device can be obtained without other access to said device.

7. A device as set forth in claim 6, in which said means permitting a flushing comprises a portion of said chamber wall means being formed of puncturable material capable of being punctured by a hollow needle means yet providing a puncture-sealing operativity when the puncturing needle is withdrawn.

8. A device for enabling determination of the time integral of the concentration of a chemical substance in a biological fluid, said device comprising:
   wall means defining a compartment, said wall means having port means defined therein with said wall means being substantially impermeable except through said port means;
   a binding composition maintained within said compartment; and
   diffusion means of known and substantially constant permittivity, said diffusion means having negligible permittivity for said binding composition, and said diffusion means being positioned at least between said port means and said binding composition so that said biological fluid contiguous to said wall means can pass through said port means and diffusion means to said compartment to be bound thereat by said binding composition.

9. The device of claim 8 wherein said wall means has a plurality of spaced ports therein, each of said plurality of spaced ports providing a separate diffusion pathway to said compartment.

10. The device of claim 9 wherein said plurality of spaced ports are provided so that no more than about one-half of the surface area of each of said ports is contained in a square region as small as one-tenth of the total surface of said wall means.

11. The device of claim 8 wherein said device is constructed of materials compatible with in vivo implantation.

12. A device for enabling determination of the time integral of the concentration of a chemical substance in a biological fluid, said chemical substance having a first fraction bound with macromolecules in said biological fluid, and said chemical substance having a second, unbound fraction, said device comprising:
   a compartment having maintainable therein a predetermined binding composition, said compartment being formed at least in part by substantially cylindrically shaped multi-layered wall means one layer of which has a plurality of port means defined therein and being substantially impermeable except through said port means, and another layer of which provides diffusion means of known and substantially constant permittivity, said diffusion means having negligible permittivity for said binding composition and for said first fraction of said chemical substance; and
   enabling means for enabling insertion and withdrawal of said binding composition from said compartment so that, when said compartment has been supplied with said binding composition and then positioned contiguous to said biological fluid, said second, unbound fraction of said chemical substance can pass through said port means and said diffusion means to said compartment to be bound by said binding composition, after which said binding composition may be withdrawn from said compartment through said enabling means.

13. The device of claim 12 wherein said one layer of said cylindrically shaped wall means has a plurality of spaced ports therein, each of said plurality of spaced ports providing a separate diffusion pathway into said compartment through said diffusion means provided by said another layer of said cylindrically shaped wall means.

14. The device of claim 13 wherein said plurality of spaced ports are provided so that no more than about one-half of the surface area of each of said ports is contained in a square region as small as one-tenth of the total surface of said wall means.

15. The device of claim 12 wherein said binding composition is prepared to maintain a concentration of said second, unbound fraction of said chemical substance within said compartment at a low value relative to the concentration of said second, unbound fraction of said chemical substance in said biological fluid.

16. The device of claim 12 wherein said binding composition is prepared to maintain a concentration of said second, unbound fraction of said chemical substance within said compartment at a value relative to said concentration of said second, unbound fraction of said chemical of substance in said biological fluid which does not result in significant reduction of the rate of diffusion across said diffusion means when said second, unbound fraction of said chemical substance is at its minimal expected concentration in said biological fluid when compared to the rate of diffusion across said diffusion means which would exist if the concentration of said second, unbound fraction of said chemical substance inside said compartment was zero.

17. The device of claim 12 wherein said enabling means includes normally closed passageways for allowing insertion and withdrawal of said binding composition while said compartment remains in vivo.

18. A device as set forth in claim 3 in which said permeable and impermeable portions of said compartment's wall means are provided by applying a permeability-reducing agent to regions other than said ports.

* * * * *